United States Patent [19]

Fogle et al.

[11] 4,421,983
[45] Dec. 20, 1983

[54] METHOD FOR MEASURING FILM THICKNESS ON WOOD PANELS USING AN IR ANALYZER

[75] Inventors: Ozzie Fogle; Harry E. Back, both of Orangeburg, S.C.

[73] Assignee: Champion International Corporation, Stamford, Conn.

[21] Appl. No.: 243,376

[22] Filed: Mar. 13, 1981

[51] Int. Cl.³ .................. G01J 1/00; G05G 15/00; B29C 23/00

[52] U.S. Cl. .................. 250/339; 250/359.1; 156/360; 264/46.4

[58] Field of Search ............ 250/338, 339, 340, 341, 250/358.1, 359.1; 156/360; 198/505; 264/40.4, 46.4

[56] References Cited

U.S. PATENT DOCUMENTS

| | | | |
|---|---|---|---|
| 3,582,428 | 6/1971 | Steinberg | 156/360 |
| 3,779,843 | 12/1973 | Knapp | 156/360 |
| 3,825,755 | 7/1974 | Ruskin | 250/339 |
| 3,930,922 | 1/1976 | Donoghue et al. | 156/360 |
| 4,097,743 | 6/1978 | Carlson | 250/339 |
| 4,243,882 | 1/1981 | Yasujima et al. | 250/339 |

OTHER PUBLICATIONS

Wood & Wood Products, "Vinyl Laminating Cuts Costs", Oct. 1980, pp. 43–44.
Brochure, Moisture Systems Corp., Model 475, Product Bulletin (two editions).

*Primary Examiner*—Janice A. Howell
*Attorney, Agent, or Firm*—Evelyn M. Sommer; John H. Mulholland; William W. Jones

[57] ABSTRACT

A method of manufacturing paneling and the like in which the thickness or weight of coatings applied to substrate materials is measured by infrared absorption providing a digital representation, accurate to 0.01 mil, of the coating's thickness or weight to 0.01 gram/sq. ft. The rate of application of the coating is adjusted in accordance with the measurement to maintain the coating weight or thickness within optimum limits.

11 Claims, 2 Drawing Figures

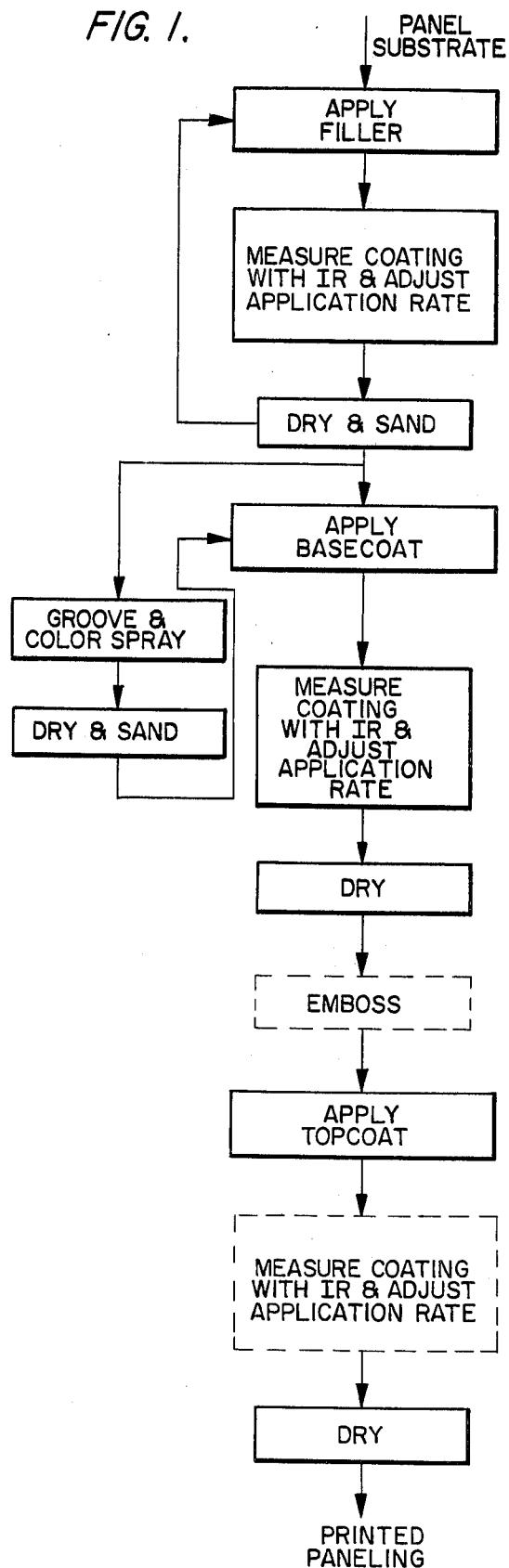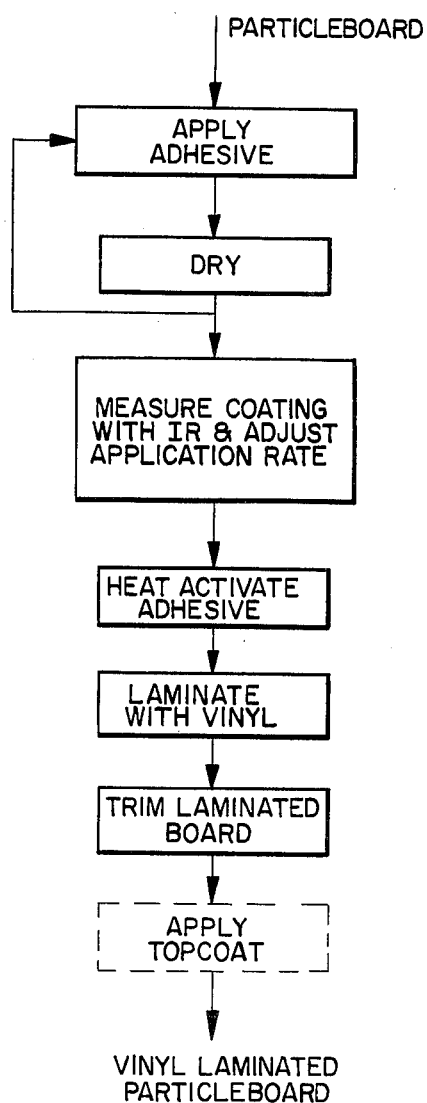

METHOD FOR MEASURING FILM THICKNESS ON WOOD PANELS USING AN IR ANALYZER

BACKGROUND OF THE INVENTION

This invention relates to a method of manufacturing paneling, siding and the like and more particularly to such method of manufacturing involving an improved method of controlling the thickness or weight of coatings applied in the manufacturing processes.

Hardwood and softwood plywood paneling and printed and painted particleboard have many uses in the construction trade. Some typical uses include household wall paneling, kitchen cabinets and desk and table tops. In addition to wood cabinets, there has been a growing trend in recent years to the manufacturing of vinyl-clad kitchen cabinets.

In the manufacture of traditional hardwood and softwood paneling and vinyl-laminated particleboards, various coatings are applied to the surface of the wood to condition the wood and prepare it for subsequent processing steps. For example, a water-based filler coating is first spread evenly over the surface of a substrate in the manufacture of printed paneling. The filler is forced into the pores in the surface of the wood mechanically and conditions the wood for the application of the base coating. In addition, a wet basecoat is later uniformly spread over the substrate. The basecoat serves as a base color for the wood substrate over which multi-head printing and/or embossing processes are used to achieve the desired color and aesthetic effect.

In the case of vinyl-laminated particleboard, an adhesive coating is applied to the wood substrate before lamination of the vinyl film onto the panel. It is important to control the exact amount of adhesive spread over the wood substrate to provide an adequate bond between the substrate and the vinyl. If an insufficient amount of adhesive is applied to the substrate, the vinyl will be easily stripped from its supporting surface and, in the more serious cases, may peel from the wood substrate.

One of the problems associated with the application of the coating materials has been the absence of an effective way to control the thickness or weight of the coating applied to the substrate. Control over the coating's thickness or weight is important to ensure a high quality product while at the same time keeping the coat of the coating material as low as possible. At the present time, the thickness or weight of the coating is roughly controlled by counting the panels that are coated for each gallon of coating material used to provide an indication of the average coating thickness or weight and making adjustments in the rate the coating material is applied in accordance with this measurement. This technique, however, fails to provide an accurate up-to-the-minute indication of each applied coating as the coating is being applied and, as a result, only a very rough control of the coating thickness is achieved.

SUMMARY OF THE INVENTION

In accordance with the present invention, an infrared analyzer compares the absorption by the coating of infrared radiation at different wavelengths to provide an accurate indication of the coating thickness or weight. The rate of application of the coating is adjusted in accordance with this measurement to thus provide an accurate control over the coating thickness or weight.

In accordance with the invention in the manufacture of wood base paneling, the thickness of a coating of filler material is measured by the infrared analyzer immediately after the filler material is applied to the substrate. If the coating thickness is outside optimum limits, the rate of application of the filler material is adjusted to bring the thickness of the coating back to within limits. Similarly, the thickness of the basecoat material is measured by an infrared analyzer immediately after the basecoat is applied to the panel substrate. If the thickness of the basecoat is outside optimum limits, the rate of application of the basecoat is adjusted to bring the thickness back within optimum limits.

In accordance with the present invention, in the manufacture of vinyl laminated particleboard, the weight of an adhesive applied to the particleboard substrate is measured by the infrared analyzer after the adhesive is dried. If the weight is outside optimum limits, the rate of application of the adhesive is adjusted to bring the weight back within limits.

The use of the infrared analyzer provides an accurate control over the thickness or weight of the applied coating materials. This accurate control of the coating provides a product with improved quality at a reduced cost. The quality is improved because the thickness of the applied coating is accurately controlled to be within optimum limits and the cost is reduced by maintaining the coating thickness or weight within optimum limits which substantially reduces the amount of coating material used. For example, in the case of the basecoat applied to wood paneling materials, the amount of basecoat material used can quite often be reduced by 20 to 25 percent while maintaining high quality in the end product.

Accordingly, among the objects of the present invention are the provision of an improved method for controlling the thickness or weight of a coating applied to a substrate material in the manufacture, finishing and laminating of paneling and siding and to thereby provide a high quality product at lower cost.

Further objects and advantages of the present invention will become apparent from the following detailed description taken in conjunction with the accompanying drawings.

BRIEF DESCRIPTION OF THE DRAWINGS

FIG. 1 is a flow chart of a process for manufacturing printed paneling; and

FIG. 2 is a flow chart of a process for the manufacture of vinyl-laminated particleboard.

DETAILED DESCRIPTION OF THE PREFERRED EMBODIMENT

FIG. 1 illustrates an example of a manufacturing process in accordance with the present invention for manufacturing a plurality of units of printed paneling. The substrate, for example, may be lauan, hardboard or particleboard. A conventional water-based filler is applied as one or more coatings to the panels by a machine such as a reverse rollcoater. The thickness of the coating of the filler material spread by the reverse rollcoaters in this step would normally be in a range from 0.1 mil to 1.2 mils. The optimum filler coating thickness after this step is 0.4 or 0.5 mils. After the wet filler coating has been applied to a panel, an infrared analyzer, which is positioned from 3 to 15 inches above the coated surface of the panel, measures the thickness of the filler coating.

The infrared analyzer utilizes the phenomenon that the coating substance strongly absorbs infrared energy at a specific wavelength and does not strongly absorb infrared energy at another wavelength. To measure the amount of a coating, the coating is irradiated with a reference wavelength, and a measurement wavelength of infrared light. The measurement wavelength is selected to be one that is not strongly absorbed by the substrate but is strongly absorbed by the coating. The infrared analyzer determines the ratio of the intensity of the reflected light at the reference wavelength to the intensity of the reflected light at the measurement wavelength. This ratio will represent the ratio of the absorption of the infrared light at the measurement wavelength to the absorption at the reference wavelength. This ratio will be an indication of the amount of absorption of the coating at the measurement wavelength and, accordingly, will correlate with the thickness or weight (amount per unit area) of the coating material. The analyzer is calibrated to provide a direct digital representation of the coating thickness.

An infrared analyzer which will perform the above described measurement is disclosed in U.S. Pat. No. 4,097,743. A commercially available infrared analyzer which will perform the above-described measurement is the Quadra-Beam TM Model 475 Analyzer manufactured and sold by Moisture Systems Corporation.

If the analyzer senses and displays its measurement of the coating thickness outside of the optimum limits of 0.4 to 0.5 mils, the rate at which the filler is being applied is adjusted to bring the coating thickness of subsequent coating steps back within the optimum thickness of the coating.

The panels are then dried and sanded before application of a second filler coating. As in the case of the first thickness measurement of the filler material, the second coating is also measured with an infrared analyzer. The film thickness range of the second filler coating would normally range from 0.1 mils to 0.8 mils. The optimum coating thickness is 0.2 to 0.4 mils. The thickness measurement of the filler is an integrated value for the surface area irradiated by the beam of infrared light as the incremental thickness varies considerably due to the porosity of the wood surface. If the thickness measurement determines that the coating thickness is outside the optimum limits, the rate of application of the second coating of filler is adjusted to bring the coating thickness back within the optimum limits.

After the second application of the filler material, as depicted in FIG. 1, the panels are dried and then the panels may be grooved and the resulting grooves color sprayed in the conventional manner.

The panels are then dried and sanded before applying a conventional basecoat. As in the case of the thickness measurement of the filler material, the thickness of the basecoat is measured with an infrared analyzer in the same manner as described above. The film thickness range of the basecoat would normally range from 0.1 mil to 1.2 mils, whereas the optimum thickness is 0.2 to 0.6 mils.

If the thickness measurement determines that the basecoat thickness is outside the optimum limits, the rate of application of the basecoat is adjusted to bring the basecoat thickness back within the optimum limits.

After applying the basecoat and drying, the panels may pass to an embossing and/or printing operation and from there to an application of a topcoat and subsequent drying to provide the finished printed paneling. The topcoat can be applied with a direct rollcoater to the panels and, as indicated in FIG. 1, the thickness of the topcoat may also be measured by an infrared analysis in the same manner as described above and the rate of application of the topcoat adjusted in accordance with the measurement to maintain a topcoat thickness within optimum limits.

FIG. 2 illustrates a flow chart of a manufacturing process for the production of vinyl-laminated particleboard. Sheets or panels of particleboard varying in thickness beginning at about ⅜" are sanded and brushed before a first application of conventional adhesive coating is applied with a direct rollcoater. After the adhesive is applied, the adhesive is dried and the combined film weight of one or more applications of adhesive coatings are measured with an infrared analyzer in the same manner as described above. The film weight would normally range from 1 gm per square foot to 12 gm per square foot, whereas the optimum weight should be 2-6 gm per square foot to ensure a strong bond to the vinyl film. If the measurement of the adhesive weight shows the weight to be outside of these optimum limit, the rate of application of the adhesive to the particleboard in the applications is adjusted to bring the adhesive weight back within the optimum limits. By monitoring the weight of adhesive spread on the particleboard, control over the vinyl lamination step is achieved, thereby reducing the number of vinyl-laminated particleboards that would have been subject to serious peeling problems or have an unnecessary costly excess of glue applied.

After measuring the weight of the adhesive coating, the boards are laminated with vinyl film using roll laminators. The laminated boards are then edge and end trimmed. The board may then be top coated with the desired topcoat material.

From the foregoing, it will be appreciated that the present invention represents an improved method for measuring the thickness or weight of a coating applied to various substrate materials. While the invention has been described in the context of a specific manufacturing process, namely, that of printed paneling and vinyl-laminated particleboard, it will be appreciated by those skilled in the art that the invention is applicable to the manufacture of other building materials in which coatings are used in the manufacturing process, such as the adhesive in plywood paneling, painted particleboard, paper laminated to particleboard, vinyl or paper laminated to hardboard or lauan, and hardboard siding. Accordingly, it is expressly intended that the foregoing description is illustrative of a preferred method only and is not limiting and that the true spirit and scope of the present invention should be determined by reference to the appended claims.

What is claimed is:

1. A method of manufacturing a plurality of printed paneling units comprising the steps of applying at least one coating of wet filler material, at a rate having a normal thickness range which includes an optimum range to a paneling substrate, sensing the thickness of the coating when wet by sensing absorption of the coating at a selected infrared wavelength to obtain a measurement representative of the thickness and amount of coating applied, and adjusting the rate of application of the filler material to the substrate in accordance with the measurement to the optimum range, then drying the coated substrate, sanding the coated surface, then applying a second coating of wet filler material, at a rate having a normal thickness range which includes an optimum range, to the coated surface, sensing the thickness of the second coating of the filler material while it is still wet by again sensing absorption of the filler material at a selected infrared wavelength to obtain a measurement representative of the accumulated thickness of the coatings applied and adjusting the rate of the application of the second coating of filler material to its optimum range in accordance with the measurement of the second coating, then drying the twice-coated substrate, then sanding the twice-coated substrate, then applying a wet basecoat to the sanded surface, at a rate having a normal thickness range which includes an optimum range, then sensing the thickness of the basecoat while it is still wet by sensing absorption of the basecoat at a selected infrared wavelength to provide a measurement representative of the thickness amount of base coating applied and adjusting the rate of application of the basecoat to its optimum range in accordance with the measurement of the thickness of said basecoat, then drying the applied basecoat, then embossing or printing the paneling with the basecoat applied, then topcoating and curing the topcoat, and then sensing the thickness of the topcoat by the amount of absorption of the topcoat material at a selected infrared wavelength.

2. A method of making a plurality of vinyl-laminated paneling units consisting of the steps of applying at least one application of adhesive, each application being at a rate having a normal range within which is an optimum range followed by drying steps of an adhesive suitable for laminating vinyl to a substrate, measuring the thickness of the combined coats of the adhesive coating by the amount of absorption of the coating of a selected infrared wavelength and adjusting the rate of application of the adhesive to the substrate in accordance with the measurement to insure that subsequent steps of applying adhesive are within the optimum range, laminating the substrate with vinyl film and proceeding with the necessary product finishing steps.

3. In a method of manufacturing a plurality of units of paneling or siding, which method includes the steps of:
 (a) providing a substrate from the group consisting of plywood, particleboard, hardboard or lauan for the finished product; and
 (b) applying at least one wet coating uniformly over a surface of the substrate for adhesive or decorative purposes, such step of applying providing a coating having a normal thickness range within which is an optimum thickness range:
 the improvement comprising a new use of a known apparatus comprising the steps of:
 (c) sensing the thickness or weight of at least one of the coatings applied in step (b) during the manufacture of the finished product by irradiating the coated substrate with a reference wavelength and a measurement wavelength of infrared light, said measurement wavelength being selected to be strongly absorbed by the coating, but not strongly absorbed by the substrate to produce a reflection of the measurement wavelength at a first intensity and a reflection of the reference wavelength at a second intensity, the ratio of said first intensity and said second intensity indicating the absorption of the coating at the measurement wavelength which ratio is representative of the thickness or weight of the coated material on said substrate, and providing an indication thereof; and
 (d) adjusting the rate of application of the coating applied in step (b) to the substrate according to said indication when the rate of application is outside of said optimum range to insure that the rate of application of the coating to the substrate will be in said optimum range in subsequently performed steps (b).

4. The method as set forth in claim 3 wherein said coating is a water-based material and the step of sensing is carried out while the coating is in a wet state on the surface of the substrate.

5. The method as set forth in claim 3 wherein the step of sensing is carried out after the coating has dried on the surface of the substrate.

6. The method as set forth in claim 5 wherein the step of coating is repeated after the coating applied in a previous step has dried, the step of sensing is carried out after the coating last applied has dried, the indication provided in the sensing step being the combined weight of the multiple application of said coating.

7. The method as set forth in claim 3 wherein the step of coating is repeated during the manufacture of said finished product and the step of sensing is repeated following each coating step.

8. The method as set forth in claim 3, wherein the finished product is printed paneling, said substrate is laun, hardboard or particle board, a first coating step is a step of applying a water-based filler having a thickness normally in the range of about 0.1 mils to about 1.2 mils with an optimum thickness of about 0.4 to 0.5 mils, and further comprising a step of drying said filler applied in said first coating step, applying a second filler coating to the dried coating-substrate combination nominally having a thickness in the range of 0.1 mils to 0.8 mils with an optimum thickness of 0.2 to 0.4 mils and again sensing the coating thickness.

9. The method as set forth in claim 7 wherein the substrate substantially comprises wood materials, and the step of sensing the thickness of the filler produces an integrated value for the surface area irradiated by the beam of infrared light to accommodate variations in the coating thickness due to the porosity of the wood surface of the substrate.

10. The method as set forth in claim 1 further including a step of applying a basecoat to the panel with a film thickness normally in the range of 0.1 to 1.2 mils, with an optimum thickness of 0.2 to 0.6 mils, followed by a step of sensing the thickness of said basecoat and adjusting the rate of application of said basecoat to reach the optimum range when said base coat thickness is outside of the optimum range.

11. The method of set forth in claim 10, further including the step of applying a topcoat to said basecoat.

* * * * *

UNITED STATES PATENT AND TRADEMARK OFFICE
CERTIFICATE OF CORRECTION

PATENT NO. : 4,421,983
DATED : December 20, 1983
INVENTOR(S) : OZZIE FOGLE and HARRY E. BACK It is certified that error appears in the above—identified patent and that said Letters Patent is hereby corrected as shown below:

Col. 1, line 49, delete "coat" and insert in lieu thereof -- cost -- ;

Col. 4, line 25, delete "limit" and insert in lieu thereof -- limits -- ;

Col. 6, line 52, delete "claim 1" and insert in lieu thereof -- claim 7 -- ;

Col. 6, line 60, delete "of" and insert in lieu thereof -- as -- .

Signed and Sealed this

Fourteenth Day of August 1984

[SEAL]

Attest:

Attesting Officer

GERALD J. MOSSINGHOFF

Commissioner of Patents and Trademarks